United States Patent
Beard et al.

(10) Patent No.: US 9,663,457 B2
(45) Date of Patent: May 30, 2017

(54) CARBAMOYL HYDRAZINE DERIVATIVES AS FORMYL PEPTIDE MODULATORS

(71) Applicant: Allergan, Inc., Irvine, CA (US)

(72) Inventors: Richard L. Beard, Newport Beach, CA (US); Vidyasagar Vuligonda, Irvine, CA (US); Thong Vu, Garden Grove, CA (US); Veena Viswanath, Irvine, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/679,510

(22) Filed: Apr. 6, 2015

(65) Prior Publication Data

US 2015/0291511 A1   Oct. 15, 2015

Related U.S. Application Data

(60) Provisional application No. 61/977,296, filed on Apr. 9, 2014.

(51) Int. Cl.
*C07C 281/06* (2006.01)

(52) U.S. Cl.
CPC .................. *C07C 281/06* (2013.01)

(58) Field of Classification Search
None
See application file for complete search history.

(56) References Cited

U.S. PATENT DOCUMENTS

| 8,541,577 B2 | 9/2013 | Beard et al. |
| 8,658,803 B2 | 2/2014 | Beard et al. |
| 8,816,076 B2 | 8/2014 | Beard et al. |
| 8,993,780 B2 | 3/2015 | Beard et al. |
| 2014/0275006 A1* | 9/2014 | Yoshinaga ........... C07D 231/12 514/210.2 |
| 2015/0148395 A1 | 5/2015 | Beard et al. |

FOREIGN PATENT DOCUMENTS

| WO | 2013-0062947 | 5/2013 |
| WO | 2013-0070600 | 5/2013 |
| WO | 2013-0158597 | 10/2013 |
| WO | 2014-0138037 | 9/2014 |
| WO | 2014-0138046 | 9/2014 |
| WO | 2015-0009545 | 1/2015 |
| WO | 2015-0077451 | 5/2015 |

OTHER PUBLICATIONS

Cross, L.C. et al, Rules for the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Migeotte, Isabelle et al., Formyl peptide receptors: A promiscuous subfamily of G protein-coupled receptors controlling immune responses, Cytokine & Growth Factor Reviews, 2006, 501-519, 17, US.
Perretti, Mauro et al, Therapeutic Anti-Inflammatory Potential of Formyl-Peptide Receptor Agonists, Pharmacology & Research, 2010, 175-188, 127.
Shao, Jie, A Novel Colorimetric and Fluorescence Anion Sensor With a Urea Group as Binding Site and a Coumarin Group as Signal Unit, 2010, 272-276(Abstract), 87(3).

* cited by examiner

*Primary Examiner* — Clinton Brooks
*Assistant Examiner* — Jennifer C Sawyer
(74) *Attorney, Agent, or Firm* — Barbara C. Potts

(57) ABSTRACT

The present invention relates to carbamoyl hydrazine derivatives, processes for preparing them, pharmaceutical compositions containing them and their use as pharmaceuticals as modulators of the FPR receptor.

11 Claims, No Drawings

CARBAMOYL HYDRAZINE DERIVATIVES AS FORMYL PEPTIDE MODULATORS

RELATED APPLICATIONS

This application claims priority to U.S. Provisional Patent Application No. 61/977,296, filed on Apr. 9, 2014, the entire disclosure of which is incorporated herein by this reference.

FIELD OF THE INVENTION

The present invention relates to carbamoyl hydrazine derivatives, processes for preparing them, pharmaceutical compositions containing them, and their use as pharmaceuticals as modulators of the N-formyl peptide receptor (FPR), including the N-formyl peptide receptor 2 (FPR2). The invention relates specifically to the use of these compounds and their pharmaceutical compositions to treat disorders associated with FPR modulation, such as FPR2 modulation.

BACKGROUND OF THE INVENTION

The FPR2 receptor is a G protein-coupled receptor that is expressed on inflammatory cells such as monocytes and neutrophils, as well as T cells, and has been shown to play a critical role in leukocyte trafficking during inflammation and human pathology. FPR2 is an exceptionally promiscuous receptor that responds to a large array of exogenous and endogenous ligands, including serum amyloid A (SAA), chemokine variant sCKβ8-1, the neuroprotective peptide human, anti-inflammatory eicosanoid lipoxin A4 (LXA4) and glucocorticoid-modulated protein annexin A1. FPR2 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists (Parmentier, Marc et al., Cytokine & Growth Factor Reviews 17 (2006) 501-519).

Activation of FPR2 by LXA4 or its analogs and by Annexin I protein has been shown to result in anti-inflammatory activity by promoting active resolution of inflammation which involves inhibition of polymorphonuclear neutrophil (PMN) and eosinophil migration and also stimulating monocyte migration, enabling clearance of apoptotic cells from the site of inflammation in a nonphlogistic manner. In addition, FPR2 has been shown to inhibit natural killer (NK) cell cytotoxicity and promote activation of T cells, which further contributes to down-regulation of tissue damaging inflammatory signals. FPR2/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPR2 thus represents an important novel pro-resolutionary molecular target for the development of new therapeutic agents in diseases with excessive inflammatory responses.

SUMMARY OF THE INVENTION

We have now discovered a group of novel compounds which are potent and selective FPR2 modulators. As such, the compounds described herein are useful in treating a wide variety of disorders associated with modulation of the FPR receptor, such as FPR2. The term "modulator" as used herein, includes but is not limited to: receptor agonist, antagonist, inverse agonist, inverse antagonist, partial agonist, partial antagonist.

This invention describes compounds of Formula I, which have FPR2 receptor biological activity. The compounds in accordance with the present invention are thus of use in medicine, for example in the treatment of humans with diseases and conditions that are alleviated by FPR modulation, such as FPR2 modulation.

In one aspect, the invention provides a compound having Formula I or the individual enantiomers, diastereoisomers, zwitterions, tautomers or a pharmaceutically acceptable salt thereof:

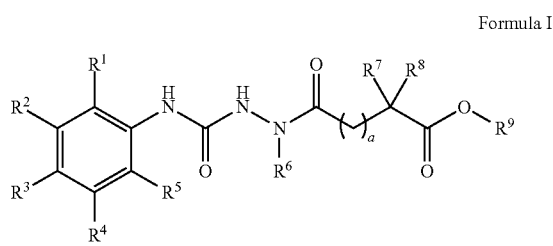

Formula I wherein:
  $R^1$ is H, optionally substituted $C_{1-6}$alkyl, $C_{1-6}$haloalkyl, optionally substituted $C_{3-8}$ cycloalkyl, optionally substituted $C_{6-10}$aryl, optionally substituted heterocycle, halogen, —$OR^{10}$, —$C_{2-6}$alkenyl, —$C_{2-6}$alkynyl, —CN, —$C(O)R^{11}$, amine, amide, urea, sulfonamide, sulfone, sulfoxide, sulfide, sulfonic acid, nitro, phosphate or phosphonic acid;
  $R^2$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$alkenyl, —$C_{2-6}$ alkynyl, —CN, —$C(O)R^{11}$, amine, amide, urea, sulfonamide, sulfone, sulfoxide, sulfide, sulfonic acid, nitro, phosphate or phosphonic acid;
  $R^3$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$alkenyl, —$C_{2-6}$alkynyl, —CN, —$C(O)R^{11}$, amine, amide, urea, sulfonamide, sulfone, sulfoxide, sulfide, sulfonic acid, nitro, phosphate or phosphonic acid;
  $R^4$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$ alkenyl, —$C_{2-6}$ alkynyl, —CN, —$C(O)R^{11}$, amine, amide, urea, sulfonamide, sulfone, sulfoxide, sulfide, sulfonic acid, nitro, phosphate or phosphonic acid;
  $R^5$ is H, optionally substituted $C_{1-6}$alkyl, $C_{1-6}$haloalkyl, optionally substituted $C_{3-8}$ cycloalkyl, optionally substituted $C_{6-10}$aryl, optionally substituted heterocycle, halogen, —$OR^{10}$, —$C_{2-6}$alkenyl, —$C_{2-6}$alkynyl, —CN, —$C(O)R^{11}$, amine, amide, urea, sulfonamide, sulfone, sulfoxide, sulfide, sulfonic acid, nitro, phosphate or phosphonic acid;
  $R^6$ is H or optionally substituted $C_{1-6}$alkyl;
  $R^7$ is H or optionally substituted $C_{1-6}$alkyl;
  $R^8$ is H or optionally substituted $C_{1-6}$alkyl;
  $R^9$ is H or optionally substituted $C_{1-6}$alkyl;
  a is 0, 1, 2 or 3;

$R^{10}$ is —OH or optionally substituted $C_{1-6}$alkyl; and
$R^{11}$ is —OH, —OC$_{1-6}$alkyl or optionally substituted $C_{1-6}$alkyl;
with the proviso that the compound of Formula I is not of structure:

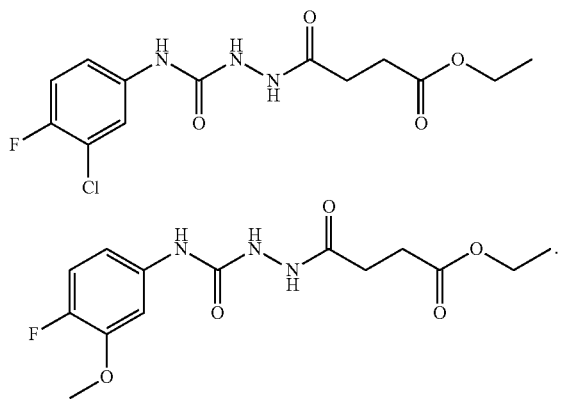 or

In another aspect, the invention provides a compound represented by Formula I, wherein:
$R^1$ is H or halogen;
$R^2$ is H or halogen;
$R^3$ is $C_{1-6}$haloalkyl or halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H or optionally substituted $C_{1-6}$alkyl;
a is 0, 1, 2 or 3;
with the proviso that the compound of Formula I is not of structure:

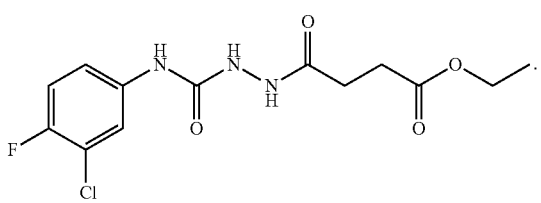 [SMILES: CCOC(=O)CCC(=O)NNC(=O)Nc1ccc(F)c(Cl)c1]

In another aspect, the invention provides a compound represented by Formula I, wherein:
$R^1$ is H or halogen;
$R^2$ is H or halogen;
$R^3$ is $C_{1-6}$haloalkyl;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H or optionally substituted $C_{1-6}$alkyl; and
a is 0, 1, 2 or 3.

In another aspect, the invention provides a compound represented by Formula I, wherein:
$R^1$ is H or halogen;
$R^2$ is H or halogen;
$R^3$ is halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H or optionally substituted $C_{1-6}$alkyl;
a is 0, 1, 2 or 3;
with the proviso that the compound of Formula I is not of structure:

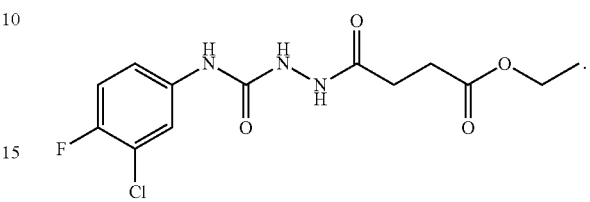

In another aspect, the invention provides a compound represented by Formula I, wherein:
$R^1$ is H or halogen;
$R^2$ is H or halogen;
$R^3$ is $C_{1-6}$haloalkyl or halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H; and
a is 0, 1, 2 or 3.

In another aspect, the invention provides a compound represented by Formula I, wherein:
$R^1$ is H or halogen;
$R^2$ is H or halogen;
$R^3$ is $C_{1-6}$haloalkyl or halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is optionally substituted $C_{1-6}$alkyl;
a is 0, 1, 2 or 3.
with the proviso that the compound of Formula I is not of structure:

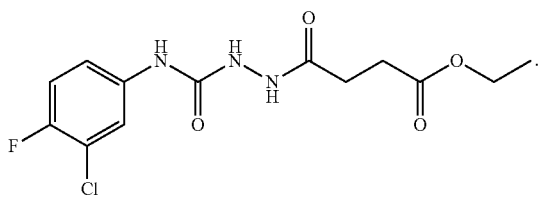 [SMILES: CCOC(=O)CCC(=O)NNC(=O)Nc1ccc(F)c(Cl)c1]

In another aspect, the invention provides a compound represented by Formula I, wherein:
$R^1$ is H or halogen;
$R^2$ is H or halogen;
$R^3$ is $C_{1-6}$haloalkyl;
$R^4$ is H or halogen;
$R^5$ is H or halogen;
$R^6$ is H or optionally substituted $C_{1-6}$ alkyl;
$R^7$ is H or optionally substituted $C_{1-6}$ alkyl;
$R^8$ is H or optionally substituted $C_{1-6}$ alkyl;
$R^9$ is H; and
a is 0, 1, 2 or 3.

In another aspect, the invention provides a compound represented by Formula I, wherein:
$R^1$ is H or halogen;
$R^2$ is H or halogen;
$R^3$ is $C_{1-6}$haloalkyl;
$R^4$ is H or halogen;
$R^5$ is H or halogen;
$R^6$ is H or optionally substituted $C_{1-6}$ alkyl;
$R^7$ is H or optionally substituted $C_{1-6}$ alkyl;
$R^8$ is H or optionally substituted $C_{1-6}$ alkyl;
$R^9$ is optionally substituted $C_{1-6}$ alkyl; and
a is 0, 1, 2 or 3.

In another aspect, the invention provides a compound represented by Formula I, wherein:
$R^1$ is H or halogen;
$R^2$ is H;
$R^3$ is halogen or $C_{1-6}$haloalkyl;
$R^4$ is H;
$R^5$ is H or halogen;
$R^6$ is H or optionally substituted $C_{1-6}$alkyl;
$R^7$ is H;
$R^8$ is H;
$R^9$ is H or optionally substituted $C_{1-6}$alkyl; and
a is 0 or 1.

In another aspect, the invention provides a compound represented by Formula I, wherein:
$R^1$ is H or halogen;
$R^2$ is H or halogen;
$R^3$ is halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H; and
a is 0, 1, 2 or 3.

In another aspect, the invention provides a compound represented by Formula I, wherein:
$R^1$ is H or halogen;
$R^2$ is H or halogen;
$R^3$ is halogen;
$R^4$ is H or halogen;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is optionally substituted $C_{1-6}$alkyl;
a is 0, 1, 2 or 3;
with the proviso that the compound of Formula I is not of structure:

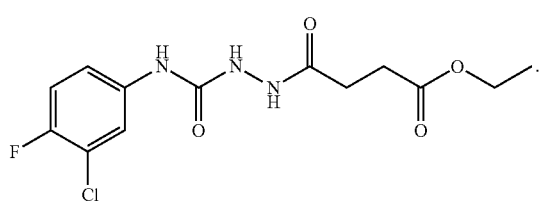 [SMILES: CCOC(=O)CCC(=O)NNC(=O)Nc1ccc(F)c(Cl)c1]

In another aspect, the invention provides a compound represented by Formula I, wherein:
$R^1$ is H or halogen;
$R^2$ is H;
$R^3$ is halogen or $C_{1-6}$haloalkyl;
$R^4$ is H;
$R^5$ is H or halogen;
$R^6$ is H or optionally substituted $C_{1-6}$alkyl;
$R^7$ is H or optionally substituted $C_{1-6}$alkyl;
$R^8$ is H or optionally substituted $C_{1-6}$alkyl;
$R^9$ is H or optionally substituted $C_{1-6}$alkyl; and
a is 0 or 1.

In another aspect, the invention provides a compound represented by Formula I, wherein:
$R^1$ is H or halogen;
$R^2$ is H;
$R^3$ is halogen or $C_{1-6}$haloalkyl;
$R^4$ is H;
$R^5$ is H or halogen;
$R^6$ is H or $C_{1-6}$alkyl;
$R^7$ is H or $C_{1-6}$alkyl;
$R^8$ is H or $C_{1-6}$alkyl;
$R^9$ is H or $C_{1-6}$alkyl; and
a is 0 or 1.

In another aspect, the invention provides a compound having Formula I, or the individual enantiomers, diastereoisomers, zwitterions, tautomers or a pharmaceutically acceptable salt thereof:

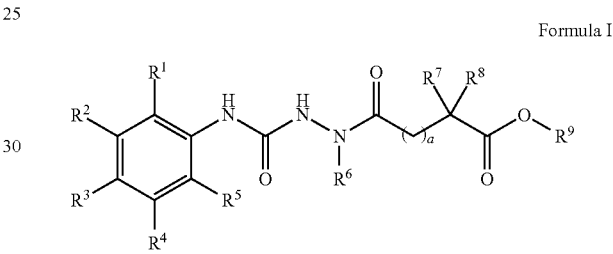

Formula I wherein:
$R^1$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$alkenyl, —$C_{2-6}$alkynyl, —CN, —$C(O)R^{11}$, amine, amide, urea, sulfonamide, sulfone, sulfoxide, sulfide, sulfonic acid, nitro, phosphate or phosphonic acid;
$R^2$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$alkenyl, —$C_{2-6}$ alkynyl, —CN, —$C(O)R^{11}$, amine, amide, urea, sulfonamide, sulfone, sulfoxide, sulfide, sulfonic acid, nitro, phosphate or phosphonic acid;
$R^3$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$alkenyl, —$C_{2-6}$alkynyl, —CN, —$C(O)R^{11}$, amine, amide, urea, sulfonamide, sulfone, sulfoxide, sulfide, sulfonic acid, nitro, phosphate or phosphonic acid;
$R^4$ is H, optionally substituted $C_{1-6}$alkyl, $C_{1-6}$haloalkyl, optionally substituted $C_{3-8}$cycloalkyl, optionally substituted $C_{6-10}$aryl, optionally substituted heterocycle, halogen, —$OR^{10}$, —$C_{2-6}$ alkenyl, —$C_{2-6}$ alkynyl, —CN, —$C(O)R^{11}$, amine, amide, urea, sulfonamide, sulfone, sulfoxide, sulfide, sulfonic acid, nitro, phosphate or phosphonic acid;
$R^5$ is H, optionally substituted $C_{1-6}$alkyl, $C_{1-6}$haloalkyl, optionally substituted $C_{3-8}$ cycloalkyl, optionally substituted $C_{6-10}$aryl, optionally substituted heterocycle, halogen, —OR$^{10}$, —C$_{2-6}$alkenyl, —C$_{2-6}$alkynyl, —CN, —C(O)R$^{11}$, amine, amide, urea, sulfonamide, sulfone, sulfoxide, sulfide, sulfonic acid, nitro, phosphate or phosphonic acid;

R$^6$ is H or optionally substituted C$_{1-6}$alkyl;
R$^7$ is H or optionally substituted C$_{1-6}$alkyl;
R$^8$ is H or optionally substituted C$_{1-6}$alkyl;
R$^9$ is H or optionally substituted C$_{1-6}$alkyl;
a is 0, 1, 2 or 3;
R$^{10}$ is —OH or optionally substituted C$_{1-6}$alkyl; and
R$^{11}$ is —OH, —OC$_{1-6}$alkyl or optionally substituted C$_{1-6}$alkyl;
provided that when a is 1, at least one of R$^6$, R$^7$ and R$^9$ is not H.

In another aspect, the invention provides a compound represented by Formula I, wherein:
R$^1$ is H or halogen;
R$^2$ is H;
R$^3$ is halogen or C$_{1-6}$haloalkyl;
R$^4$ is H;
R$^5$ is H or halogen;
R$^6$ is H or optionally substituted C$_{1-6}$alkyl;
R$^7$ is H or optionally substituted C$_{1-6}$alkyl;
R$^8$ is H or optionally substituted C$_{1-6}$alkyl;
R$^9$ is H or optionally substituted C$_{1-6}$alkyl; and
a is 0 or 1;
provided that when a is 1, at least one of R$^6$, R$^7$ and R$^9$ is not H.

In another aspect, the invention provides a compound represented by Formula I, wherein:
R$^1$ is H or halogen;
R$^2$ is H;
R$^3$ is halogen or C$_{1-6}$haloalkyl;
R$^4$ is H;
R$^5$ is H or halogen;
R$^6$ is H or C$_{1-6}$alkyl;
R$^7$ is H or C$_{1-6}$alkyl;
R$^8$ is H or C$_{1-8}$alkyl;
R$^9$ is H or C$_{1-8}$alkyl; and
a is 0 or 1;
provided that when a is 1, at least one of R$^6$, R$^7$ and R$^9$ is not H.

The term "alkyl", as used herein, refers to saturated, monovalent or divalent hydrocarbon moieties having linear or branched moieties or combinations thereof and containing 1 to 6 carbon atoms (i.e., C$_{1-6}$alkyl). One or more methylene (CH$_2$) groups of the alkyl can be replaced by oxygen, sulfur, carbonyl, sulfoxide, sulfonyl, or by a divalent C$_{3-6}$cycloalkyl. One or more methine (CH) groups of the alkyl can be replaced by nitrogen. Alkyl groups are optionally substituted with one or more groups including, but not limited to: halogen, hydroxyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "cycloalkyl", as used herein, refers to a monovalent or divalent group of 3 to 8 carbon atoms (i.e., C$_{3-8}$cycloalkyl) derived from a saturated cyclic hydrocarbon. Cycloalkyl groups can be monocyclic or polycyclic. Cycloalkyl groups are optionally substituted with one or more groups including, but not limited to: halogens, hydroxyls, cycloalkyls, heterocycles, aryls, ethers, amines, nitros, nitriles, amides, sulfonamides, esters, aldehydes, carboxylic acids, ketones, sulfonic acids, phosphonic acids, phosphoric acids.

The term "cycloalkenyl", as used herein, refers to a monovalent or divalent group of 3 to 8 carbon atoms (i.e., C$_{3-8}$cycloalkenyl) derived from a saturated cycloalkyl having one or more double bonds. Cycloalkenyl groups can be monocyclic or polycyclic. Cycloalkenyl groups are optionally substituted by one or more groups including, but not limited to halogens, hydroxyls, cycloalkyls, heterocycles, aryls, ethers, amines, nitros, nitriles, amides, sulfonamides, esters, aldehydes, carboxylic acids, ketones, sulfonic acids, phosphonic acids, phosphoric acids.

The term "halogen", as used herein, refers to an atom of chlorine, bromine, fluorine, iodine.

The term "alkenyl", as used herein, refers to a monovalent or divalent hydrocarbon radical having 2 to 6 carbon atoms (i.e., C$_{2-6}$ alkenyl), derived from a saturated alkyl, having at least one double bond. C$_{2-6}$ alkenyl can be in the E or Z configuration. Alkenyl groups are optionally substituted with C$_{1-3}$alkyl.

The term "alkynyl", as used herein, refers to a monovalent or divalent hydrocarbon radical having 2 to 6 carbon atoms (i.e., C$_{2-6}$ alkynyl) derived from a saturated alkyl, having at least one triple bond.

The term "heterocycle" as used herein, refers to a 3 to 10 membered ring, which can be aromatic or non-aromatic, saturated or non-saturated, containing at least one heteroatom selected from O, N and S, or combinations of at least two thereof, interrupting the carbocyclic ring structure. The heterocyclic ring can be interrupted by one or more C=O; the S heteroatom can be oxidized. Heterocycles can be monocyclic or polycyclic. Heterocyclic ring moieties are optionally substituted with one or more groups including, but not limited to: halogens, hydroxyls, cycloalkyls, heterocycles, aminos, nitros, nitriles, amides, ethers, esters, ketones, carboxylic acids, aldehydes, sulfonamides, sulfonic acids, phosphonic acids, phosphoric acids.

The term "aryl" as used herein, refers to an organic moiety derived from an aromatic hydrocarbon consisting of a ring containing 6 to 10 carbon atoms by removal of one hydrogen (i.e., C$_{6-10}$aryl). Aryl groups are optionally substituted by one or more groups including, but not limited to: halogens, hydroxyls, cycloalkyls, heterocycles, aminos, nitros, nitriles, amides, ethers, esters, carboxylic acids, aldehydes, ketones, sulfonamides sulfonic acids, phosphonic acids, phosphoric acids. Aryl can be monocyclic or polycyclic.

The term "amine" as used herein, represents a group of formula "—NR$^x$R$^y$", wherein R$^x$ and R$^y$ can be the same or independently H, alkyl, aryl, cycloalkyl, cycloalkenyl or heterocyclyl, as defined above.

The term "amide" as used herein, represents a group of formula "—C(O)N(R$^x$)(R$^y$)" or "—NR$^x$C(O)R$^y$" wherein R$^x$ and R$^y$ can be the same or independently H, alkyl, aryl, cycloalkyl, cycloalkenyl or heterocyclyl, as defined above.

The term "sulfonamide" as used herein, represents a group of formula "—S(O)$_2$N(R$^x$)(R$^y$)" or "—NR$^x$S(O)$_2$R$^y$" wherein R$^x$ and R$^y$ can be the same or independently H, alkyl, aryl, cycloalkyl, cycloalkenyl or heterocyclyl, as defined above.

The term "ester" as used herein, represents a group of formula "—C(O)O(R$^x$)", wherein R$^x$ is alkyl, aryl, cycloalkyl, cycloalkenyl or heterocyclyl, as defined above.

The term "aldehyde" as used herein, represents a group of formula "—C(O)H".

The term "ketone" as used herein, represents a group of formula "—C(O)R$^x$" wherein R$^x$ is alkyl, aryl, cycloalkyl, cycloalkenyl or heterocyclyl, as defined above.

The term "hydroxyl" as used herein, represents a group of formula "—OH".

The term "amino" as used herein, represents a group of formula "—NH$_2$".

The term "carbonyl" as used herein, represents a group of formula "—C(O)—".

The term "carboxyl" as used herein, represents a group of formula "—C(O)O—".

The term "sulfonyl" as used herein, represents a group of formula "—SO$_2$—".

The term "sulfate" as used herein, represents a group of formula "—OS(O)$_2$O$^-$".

The term "carboxylic acid" as used herein, represents a group of formula "—C(O)OH".

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The term "nitro" as used herein, represents a group of formula "—NO$_2$".

The term "nitrile" as used herein, represents a group of formula "—CN".

The term "ether" as used herein, represents a group of formula "—OR$^x$, wherein R$^x$ is alkyl, aryl, cycloalkyl, cycloalkenyl or heterocyclyl, as defined above.

Some compounds of the invention are:
4-{2-[(4-Bromo-2-fluorophenyl)carbamoyl]-1-propylhydrazinyl}-4-oxobutanoic acid;
Ethyl 4-{2-[(4-bromo-2-fluorophenyl)carbamoyl]-1-propylhydrazinyl}-4-oxobutanoate;
Ethyl 4-{2-[(4-bromophenyl)carbamoyl]-1-butylhydrazinyl}-4-oxobutanoate;
4-[1-(2-Methylpropyl)-2-{[4-(trifluoromethyl)phenyl]carbamoyl}hydrazinyl]-4-oxobutanoic acid;
4-oxo-4-(1-Propyl-2-{[4-(trifluoromethyl)phenyl]carbamoyl}hydrazinyl)butanoic acid;
Ethyl 4-[1-(2-methylpropyl)-2-{[4-(trifluoromethyl)phenyl]carbamoyl}hydrazinyl]-4-oxobutanoate;
Ethyl 4-oxo-4-(1-propyl-2-{[4-(trifluoromethyl)phenyl]carbamoyl}hydrazinyl) butanoate;
4-{2-[(4-Bromo-2-fluorophenyl)carbamoyl]-1-(2-methylpropyl)hydrazinyl}-4-oxobutanoic acid;
Ethyl 4-{2-[(4-bromo-2-fluorophenyl)carbamoyl]-1-(2-methylpropyl)hydrazinyl}-4-oxobutanoate;
4-{2-[(4-Bromophenyl)carbamoyl]-1-(2-methylpropyl)hydrazinyl}-4-oxobutanoic acid;
Ethyl 4-{2-[(4-bromophenyl)carbamoyl]-1-(2-methylpropyl)hydrazinyl}-4-oxobutanoate;
4-{2-[(4-Bromophenyl)carbamoyl]hydrazinyl}-2,2-diethyl-4-oxobutanoic acid;
2-(2-{2-[(4-Bromophenyl)carbamoyl]hydrazinyl}-2-oxoethyl)-2-propylpentanoic acid;
Methyl 2-(2-{2-[(4-Bromophenyl)carbamoyl]hydrazinyl}-2-oxoethyl)-2-propylpentanoate;
4-{2-[(4-Bromophenyl)carbamoyl]hydrazinyl}-2,2-dimethyl-4-oxobutanoic acid;
3-{2-[(4-Bromophenyl)carbamoyl]hydrazinyl}-2,2-dimethyl-3-oxopropanoic acid; and
Ethyl 3-{2-[(4-Bromophenyl)carbamoyl]hydrazinyl}-3-oxopropanoate.

Some compounds of Formula I and some of their intermediates have at least one asymmetric center in their structure. This asymmetric center may be present in an R or S configuration, said R and S notation corresponding to the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

The compounds of the invention are indicated for use in treating or preventing conditions in which there is likely to be a component involving the FPR, including FPR2.

In another embodiment, there are provided pharmaceutical compositions including at least one compound of the invention in a pharmaceutically acceptable carrier.

In a further embodiment of the invention, there are provided methods for treating disorders associated with modulation of the FPR, including FPR2. Such methods can be performed, for example, by administering to a subject in need thereof a pharmaceutical composition containing a therapeutically effective amount of at least one compound of the invention.

Therapeutic utilities of the FPR modulators, including those which modulate FPR2, are ocular inflammatory diseases including, but not limited to, wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, corneal wound healing burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by FPR modulation (such as FPR2 modulation): including, but not limited to the treatment of ocular inflammatory diseases: wet and dry age-related macular degeneration (ARMD), dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, and chorioditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, corneal wound healing, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE.

In still another embodiment of the invention, there are provided methods for treating disorders associated with modulation of the FPR receptor, such as modulation of the FPR2 receptor. Such methods can be performed, for example, by administering to a subject in need thereof a therapeutically effective amount of at least one compound of the invention, or any combination thereof, or pharmaceutically acceptable salts, individual enantiomers, and individual diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; infectious keratitis, herpetic keratitis, corneal angiogenesis, lymphangiogenesis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, corneal wound healing, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose, any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene. Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses. Especially preservative-free solutions are often formulated in non-resalable containers containing up to about ten, preferably up to about five units doses, where a typical unit dose is from one to about 8 drops, preferably one to about 3 drops. The volume of one drop usually is about 20-35 μl.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the FPR receptor, such as FPR2. Thus, in further embodiments of the invention, there are provided methods for treating a disorder associated with modulation of the FPR receptor, such as modulation of the FPR2 receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry. Synthetic Scheme 1, set forth below, illustrates how the compounds according to the invention can be made.

Scheme 1. General method for synthesis of compounds of Formula I.

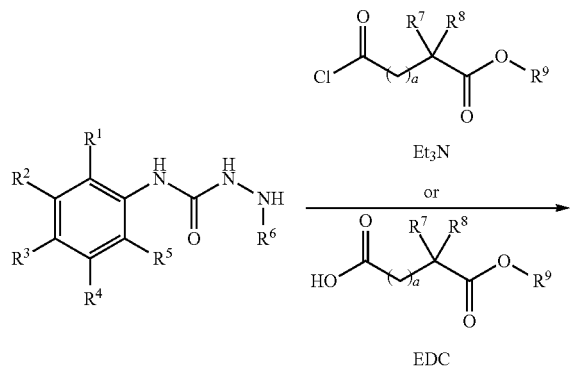

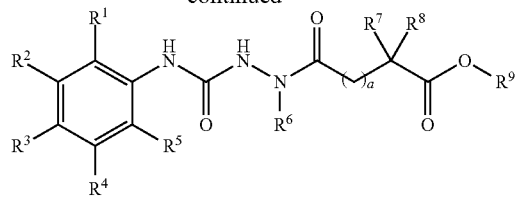

Compounds within the scope of the invention may be prepared as depicted in Scheme 1. In general, a N-arylhydrazinecarboxamide can be alkylated with an aldehyde under reductive amination conditions (e.g., NaCNBH$_3$) to produce a N'-substituted N-arylhydrazinecarboxamide. This compound (or an unsubstituted N-arylhydrazinecarboxamide) can be treated with an appropriately substituted acid chloride in the presence of a base or a substituted carboxylic acid in the presence of a coupling agent like EDC to provide compounds of Formula I.

At this stage, those skilled in the art will appreciate that many additional compounds that fall under the scope of the invention covered by Formula I may be prepared by performing various common chemical reactions. Details of certain specific chemical transformations are provided in the Examples that follow. Those skilled in the art will be able to routinely modify and/or adapt the schemes to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and mixtures thereof, including racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following Examples are for illustrative purposes only and are not intended, nor should they be construed as limiting the invention in any manner. Those skilled in the art will appreciate that variations and modifications of the following Examples can be made without exceeding the spirit or scope of the invention.

As will be evident to those skilled in the art, individual diastereoisomeric forms can be obtained by separation of mixtures thereof in a conventional manner. For example, chromatographic separation may be employed; chiral chromatography may be performed to separate individual enantiomers.

Compound names were generated with ACDLab version 12.5; some intermediates' and reagents' names used in the examples were generated with softwares such as Chem Bio Draw Ultra version 12.0, ACDLab version 12.5 or Auto Nom 2000 from MDL ISIS Draw 2.5 SP1.

In general, characterization of the compounds was performed using NMR spectra, which were recorded on a 300 or 600 MHz Varian NMR spectrometer and acquired at room temperature. Chemical shifts are given in ppm referenced either to internal TMS or to the solvent signal. All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, ChemImpex, MIC-scientific, Ltd; however some known intermediates, were prepared according to published procedures.

Usually the compounds of the invention were purified by column chromatography (Auto-column) on Teledyne-ISCO CombiFlash with a silica column, unless noted otherwise.

The following abbreviations are used in the examples:
THF tetrahydrofuran
CD$_3$OD deuterated methanol
RT room temperature
CH$_2$Cl$_2$ dichloromethane
EtOAc ethyl acetate
EtOH ethanol
Et$_3$N triethylamine
DMSO-D6 deuterated dimethylsulfonamide
K$_2$CO$_3$ potassium carbonate
HCl hydrochloric acid
CD$_3$CN deuterated acetonitrile
NaCNBH$_3$ sodium borohydride
EtOAc ethyl acetate
NaHCO$_3$ sodium bicarbonate
AcOH acetic acid
CDCl$_3$ deuterated chloroform
TLC thin layer chromatography
EDC 1-Ethyl-3-(3-dimethylaminopropyl)carbodiimide
HOBT 1H-benzotriazol-1-ol
LiOH lithium hydroxide
H$_2$O water
KOH potassium hydroxide Example 1

Intermediate 1

(E)-N-(4-Bromophenyl)-2-(2-methylpropylidene)hydrazinecarboxamide

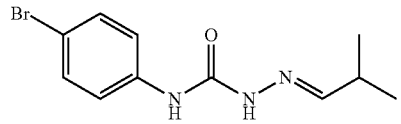 [SMILES: CC(C)/C=N/NC(=O)Nc1ccc(Br)cc1]

A mixture of N-(4-bromophenyl)-hydrazinecarboxamide CAS#2646-26-6 (231 mg, 1 mmol), isobutyraldehyde CAS#78-84-2 (86 mg, 1.2 mmol), K$_2$CO$_3$ (304 mg, 1.2 mmol) in THF (5 mL) was stirred for 2 h. The reaction mixture was diluted with EtOAc (15 mL), washed with dilute aq. HCl (0.5% solution, 5 mL). The EtOAc layer was dried and the solvent was removed. Intermediate 1 was isolated as a white solid.

$^1$HNMR (CD$_3$CN) δ: 1.12 (d, J=7.0 Hz, 6H), 2.48-2.59 (m, 1H), 7.18 (d, J=4.98 Hz, 1H), 7.42-7.53 (m, 4H).

Intermediates 3, 5, 7 and 9 were prepared from the corresponding hydrazinecarboxamides and aldehydes, in a similar manner to the procedure described in Example 1 for Intermediate 1. The results are described below in Table 1.

TABLE 1

| Intermediate No. | IUPAC name Structure | Hydrazine carboxamide | Aldehyde |
| --- | --- | --- | --- |
| 3 | (E)-N-(4-bromo-2-fluorophenyl)-2-(2 methylpropylidene)hydrazinecarboxamide | N-(4-bromo-2-fluorophenyl)-hydrazinecarboxamide CAS 1094561-48-4 | Isobutyraldehyde CAS 78-84-2 |
| 5 | (E)-2-(2-methylpropylidene)-N-(4-(trifluoromethyl)phenyl)hydrazinecarboxamide | N-[4-(trifluoromethyl)phenyl]-hydrazinecarboxamide CAS 131210-52-1 | Isobutyraldehyde CAS 78-84-2 |

TABLE 1-continued

| Intermediate No. | IUPAC name Structure | Hydrazine carboxamide | Aldehyde |
|---|---|---|---|
| 7 | (E)-2-propylidene-N-(4-(trifluoromethyl)phenyl)hydrazinecarboxamide | N-[4-(trifluoromethyl)phenyl]-hydrazinecarboxamide CAS 131210-52-1 | Propanal CAS 123-38-6 |
| 9 | (E)-N-(4-bromophenyl)-2-butylidenehydrazinecarboxamide | N-(4-bromophenyl)hydrazinecarboxamide CAS 2646-26-6 | Butanal CAS 123-72-8 |

Example 2

Intermediate 2

N-(4-Bromophenyl)-2-isobutylhydrazinecarboxamide

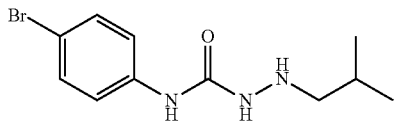

To a mixture of Intermediate 1 (580 mg, 2.05 mmol) and NaCNBH$_3$ (196 mg, 3.1 mmol) in THF (8 mL) was added AcOH (326 mg, 4.1 mmol) and stirred at RT for 6 h. All of the solvent was removed and the crude mixture was dissolved in EtOAc (50 mL), washed with aq. NaHCO$_3$ (10% solution, 10 mL), brine, dried and the solvent was removed. The crude mixture was purified by silica gel chromatography, using EtOAc in hexane as eluent. Intermediate 2 was isolated as a white solid.

$^1$HNMR (CD$_3$CN) δ: 0.97 (d, J=6.7 Hz, 6H), 1.75-1.87 (m, 1H), 2.61 (d, J=6.7 Hz, 2H), 7.38 (s, 4H).

Intermediates 4, 6, 8 and 10 were prepared from in a similar manner to the procedure described in Example 2 for Intermediate 2. The results are described below in Table 2.

TABLE 2

| Interm. No. | IUPAC name Structure | From Interm. No. | $^1$H NMR δ (ppm) |
|---|---|---|---|
| 4 | N-(4-bromo-2-fluorophenyl)-2-isobutylhydrazinecarboxamide | 3 | $^1$HNMR (CDCl$_3$): δ 0.98 (d, J = 6.1 Hz, 6H), 1.70-1.85 (m, 1H), 2.68 (t, J = 6.1 Hz, 2H), 7.13-7.18 (m, 2H), 8.18 (t, J = 8.6 Hz, 1H). |
| 6 | 2-isobutyl-N-(4-(trifluoromethyl)phenyl)hydrazinecarboxamide | 5 | $^1$HNMR (CD$_3$OD): δ 0.96 (d, J = 6.7 Hz, 6H), 1.70-1.86 (m, 1H), 2.62 (d, J = 7.0 Hz, 2H), 7.50-7.66 (m, 4H). |

TABLE 2-continued

| Interm. No. | IUPAC name Structure | From Interm. No. | $^1$H NMR δ (ppm) |
|---|---|---|---|
| 8 | 2-propyl-N-(4-(trifluoromethyl)phenyl)hydrazinecarboxamide | 7 | $^1$HNMR (CD$_3$OD): δ 1.05 (t, J = 7.0 Hz, 3H), 1.64-1.82 (m, 2H), 3.07-3.24 (m, 2H), 7.49-7.64 (m, 2H), 7.64-7.76 (m, 2H). |
| 10 | N-(4-bromophenyl)-2-butylhydrazinecarboxamide | 9 | $^1$HNMR (CD$_3$OD): δ 0.94 (t, J = 7.0 Hz, 3H), 1.30-1.60 (m, 4H), 2.80 (t, J = 7.0 Hz, 2H), 7.38 (s, 4H). |
| 11 | N-(4-Bromo-2-fluorophenyl)-2-propylhydrazinecarboxamide | N-(4-bromo-2-fluorophenyl)-hydrazine carboxamide CAS 1094561-48-4 Propanal CAS 123-38-6 | $^1$HNMR (CD$_3$OD) δ 0.98 (t, J = 7.5 Hz, 3H), 1.37-1.71 (m, 2H), 2.78 (t, J = 7.0 Hz, 2H), 7.07-7.46 (m, 2H), 7.88-8.17 (m, 1H). |

Example 3

Compound 1

Ethyl 3-{2[(4-bromophenyl)carbamoyl]hydrazinyl}-3-oxopropanoate

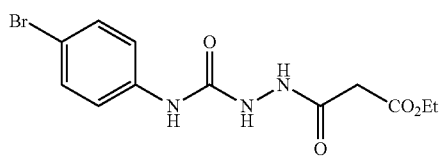 [SMILES: CCOC(=O)CC(=O)NNC(=O)Nc1ccc(Br)cc1]

To a solution of N-(4-bromophenyl)hydrazinecarboxamide (CAS#2646-26-6; 100 mg, 0.44 mmol), and Et$_3$N (88 mg, 0.88 mmol) in CH$_2$Cl$_2$ (3 mL) and DMF (1 mL) was added 3-chloro-3-oxo-propanoic acid ethyl ester (CAS#36239-09-5; 75 mg, 0.5 mmol). The mixture was stirred at RT for 18 h; then the solvent was removed, and the crude mixture was purified by preparative TLC. Compound 1 was isolated as a white solid.

$^1$HNMR (CD$_3$OD) δ: 1.35 (t, J=7.5 Hz, 3H), 3.31 (s, 2H), 4.25 (q, J=7.5 Hz, 2H), 7.40 (s, 4H).

Example 4

Compound 2

3-{2-[(4-Bromophenyl)carbamoyl]hydrazinyl}-2,2-dimethyl-3-oxopropanoic Acid

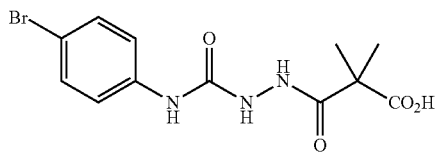 [SMILES: CC(C)(C(=O)O)C(=O)NNC(=O)Nc1ccc(Br)cc1]

A mixture of N-(4-bromophenyl)hydrazinecarboxamide (CAS#2646-26-6; 100 mg, 0.44 mmol), EDC (130 mg, 0.66 mmol), HOBT (90 mg, 0.66 mmol), 4-methyl morpholine (131 mg, 1.32 mmol) and dimethylmalonic acid (58 mg, 0.44 mmol) in CH$_2$Cl$_2$ (5 mL) was stirred at RT for 18 h. The solvent was removed and the crude mixture was purified by preparative TLC. Compound 2 was isolated as a white solid.

$^1$HNMR (CD$_3$OD) δ: 1.31 (s, 6H), 7.42 (br s, 4H).

Compounds 3, 4 and 6 were prepared in a similar manner to the procedure described in Example 4 for Compound 2. The results are shown below in Table 3.

TABLE 3

| Cmpd. No. | IUPAC name Structure | Starting materials | $^1$H NMR δ (ppm) |
|---|---|---|---|
| 3 | 4-{2-[(4-bromophenyl)carbamoyl]hydrazinyl}-2,2-dimethyl-4-oxobutanoic acid | N-(4-bromophenyl)hydrazinecarboxamide CAS 2646-26-6 2,2-dimethyl Butanedioic acid CAS 597-43-3 | $^1$HNMR (CD$_3$OD) δ: 1.38 (s, 6H), 2.68 (s, 2H), 7.35 (d, J = 8.2 Hz, 2H), 7.40 (d, J = 8.2 Hz, 2H). white solid |
| 4 | methyl 2-(2-{2-[(4-bromophenyl)carbamoyl]hydrazinyl}-2-oxoethyl)-2-propylpentanoate | N-(4-bromophenyl)hydrazinecarboxamide CAS 2646-26-6 butanedioic acid, 2,2-dipropyl-,1-methyl ester CAS 664304-90-9 | $^1$HNMR (CD$_3$OD) δ: 0.91 (br s, 6H), 1.16-1.36 (m, 4H), 1.59-1.75 (m, 4H), 2.57 (s, 2H), 3.67 (s, 3H), 7.38 (s, 4H). |
| 6 | 4-{2-[(4-bromophenyl)carbamoyl]hydrazinyl}-2,2-diethyl-4-oxobutanoic acid | N-(4-bromophenyl)hydrazinecarboxamide CAS 2646-26-6 3,3-diethyldihydro-2,5-Furandione CAS 2840-69-9 | $^1$HNMR (CD$_3$OD) δ: 0.91 (t, J = 7.5 Hz, 6H), 1.76 (q, J = 7.5 Hz, 2H), 2.53 (s, 2H), 7.37 (m, 4H). |

Example 5

Compound 5

2-[2-(2-{[(4-Bromophenyl)amino]carbonyl}hydrazino)-2-oxoethyl]-2-propylpentanoic Acid

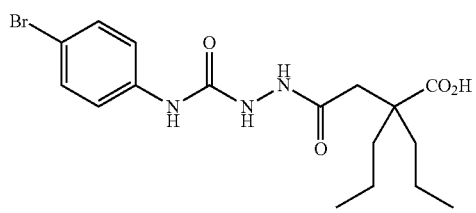 [SMILES: CCCC(CCC)(CC(=O)NNC(=O)Nc1ccc(Br)cc1)C(=O)O]

A mixture of Compound 4 (280 mg, 0.65 mmol) LiOH—H$_2$O (1 M solution, 2, mL) and methanol (5 mL) was stirred for 5 h at RT. The reaction was quenched with 10% HCl solution (2 mL), extracted with EtOAC, the organic layer was washed with brine, dried and solvent removed. The crude product was purified by preparative TLC. Compound 5 was isolated as a light yellow solid.

$^1$HNMR (CD$_3$OD) δ: 0.93 (br s, 6H), 1.29 (br s, 4H), 1.65 (br s, 4H), 2.70 (br s, 2H), 7.23-7.51 (m, 4H).

Example 6

Compound 7

Ethyl 4-{2-[(4-Bromophenyl)carbamoyl]-1-(2-methylpropyl)hydrazinyl}-4-oxobutanoate

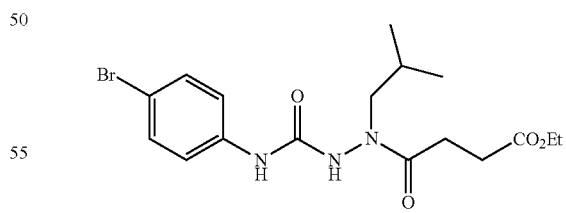

To a cold (0° C.) mixture of Intermediate 2 (183 mg, 0.63 mmol), Et$_3$N (77 mg, 0.77 mmol) in dioxane (4 mL) was added 4-chloro-4-oxo-butanoic acid ethyl ester (CAS#14794-31-1; 115 mg, 0.69 mmol). The mixture was stirred at RT for 2 h. The reaction was diluted with EtOAc (50 mL), washed with aq. NaHCO$_3$ (10 mL), dried and solvent removed. The crude product was recrystallized from hot methanol. Compound 7 was isolated as a white solid.

¹HNMR (CD₃CN): δ 0.93 (br d, 6H), 1.23 (t, J=7.3 Hz, 3H), 1.82-1.95 (m, 1H), 2.54 (t, J=6.1 Hz, 2H), 2.62 (br. d, 2H), 2.78 (t, J=6.1 Hz, 2H), 4.12 (q, J=7.3 Hz, 2H), 7.37-7.49 (m, 4H).

Compounds 9, 11, 13, 15 and 16 were prepared in a similar manner to the procedure described in Example 6 for Compound 7. The results are described below in Table 4.

TABLE 4

| Compound No. | IUPAC name Structure | Interm. No | ¹H NMR δ (ppm) |
|---|---|---|---|
| 9 | ethyl 4-{2-[(4-bromo-2-fluorophenyl)carbamoyl]-1-(2-methylpropyl)hydrazinyl}-4-oxobutanoate | 4 | ¹HNMR (CD3OD): δ 0.91 (br. S, 6H), 1.21 (t, J = 7.2 Hz, 3H), 1.82-2.05 (m, 1H), 2.50-2.70 (br. S, 4H), 2.75-3.00 (br. s, 2H), 4.09 (q, J = 7.2 Hz, 2H), 7.20-7.35 (m, 2H), 7.90 (br. t, 1H). |
| 11 | ethyl 4-[1-(2-methylpropyl) 2{[4-(trifluoromethyl)phenyl]carbamoyl}hydrazinyl]-4-oxobutanoate | 6 | ¹HNMR (CD₃OD): δ 0.93 (br. S, 6H), 1.23 (t, J = 7.2 Hz, 3H), 1.90-2.05 (m, 1H), 2.50-2.70 (br. S, 4H), 2.75-3.00 (br. s, 2H), 4.12 (q, J = 7.2 Hz, 2H), 7.47-7.75 (m, 4H). |
| 13 | ethyl 4-oxo-4-(1-propyl-2-{[4-(trifluoromethyl)phenyl]carbamoyl}hydrazinyl)butanoate | 8 | ¹HNMR (CD₃OD): δ 0.92 (t, J = 7.3 Hz, 3H), 1.24 (t, J = 7.0 Hz, 3H), 1.45-1.71 (m, 2H), 2.50-2.82 (br. s, 4H), 3.30-3.40 (br. s, 2H), 4.12 (q, J = 7.0 Hz, 2H), 7.46-7.74 (m, 4H). |
| 15 | ethyl 4-{2-[(4-bromophenyl)carbamoyl]-1-butylhydrazinyl}-4-oxobutanoate | 10 | ¹HNIMR (CD₃OD): δ 0.93 (t, J = 7.2 Hz, 3H), 1.23 (t, J = 7.2 Hz, 3H), 1.30-1.40 (m, 2H), 1.50-1.62 (m, 2H), 2.50-2.70 (br. s, 4H), 2.70-2.90 (br. s, 2H), 4.12 (q, J = 7.2 Hz, 2H), 7.40 (s, 4H). |

TABLE 4-continued

| Compound No. | IUPAC name Structure | Interm. No | $^1$H NMR δ (ppm) |
|---|---|---|---|
| 16 | ethyl 4-{2-[(4-bromo-2-fluorophenyl)carbamoyl]-1-propylhydrazinyl}-4-oxobutanoate | Intermediate 11 | $^1$HNMR (CD$_3$OD): δ 0.91 (t, J = 7.3 Hz, 3H), 1.22 (t, J = 7.2 Hz, 3H), 1.55-1.70 (m, 2H), 2.50-2.80 (br s, 4H), 3.20-3.40 (br s, 2H), 4.10 (q, J = 7.2 Hz, 2H), 7.26 (dd, J = 1.2, 8.8 Hz, 1H), 7.33 (dd, J = 2.1, 10.6 Hz, 1H), 7.87 (br s, 1H). |

Example 7

Compound 8

4-{2-[(4-Bromophenyl)carbamoyl]-1-(2-methylpropyl)hydrazinyl}-4-oxobutanoic Acid

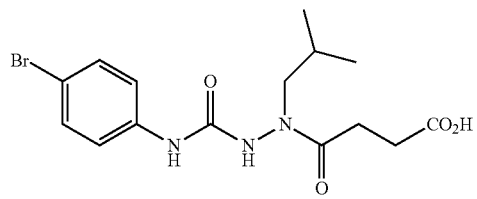 [SMILES: CC(C)CN(NC(=O)Nc1ccc(Br)cc1)C(=O)CCC(=O)O]

A mixture of Compound 7 (90 mg, 0.22 mmol), KOH—H$_2$O (1 M solution, 1 mL), EtOH (1 mL) and dioxane (1 mL) was stirred at RT for 3 h. About 80% of the solvent was removed, the crude mixture cooled to −78° C. and acidified with aq. HCl. Compound 8 was collected as a white solid.

$^1$HNMR (DMSO-D$_6$): δ 0.93 (br s, 6H), 1.82-1.99 (m, 1H), 2.53 (br. s, 2H), 2.85 (br. s, 2H), 2.30 (br. s, 2H), 7.55 (s, 4H).

Compounds 10, 12, 14 and 17 were prepared in a similar manner to the procedure described in Example 7 for Compound 8. The results are described below in Table 5.

TABLE 5

| Compound No. | IUPAC name Structure | Starting Compound | $^1$H NMR δ (ppm) |
|---|---|---|---|
| 10 | 4-{2-[(4-bromo-2-fluorophenyl)carbamoyl]-1-(2-methylpropyl)hydrazinyl}-4-oxobutanoic acid | 9 | $^1$HNMR (CD$_3$OD): δ 0.91 (br. S, 6H), 1.94 (br. s, 1H), 2.57 (br. S, 4H), 2.98 (br. s, 2H), 7.20-7.35 (m, 2H), 7.87 (br. t, 1 H). |
| 12 | 4-[1-(2-methylpropyl)-2-{[4-(trifluoromethyl)phenyl]carbamoyl}hydrazinyl]-4-oxobutanoic acid | 11 | $^1$HNMR (CD$_3$OD): δ 0.92 (br. s, 6H), 1.92-2.02 (m, 1H), 2.45-2.65 (br. s, 4H), 2.70-2.80 (br., s, 2H), 7.54 (d, J = 8.2 Hz, 2H), 7.65 (d, J =8.2 Hz, 2H). |

TABLE 5-continued

| Compound No. | IUPAC name Structure | Starting Compound | $^1$H NMR δ (ppm) |
|---|---|---|---|
| 14 | 4-oxo-4-(1-propyl-2-{[4-(trifluoromethyl)phenyl]carbamoyl} hydrazinyl)butanoic acid | 13 | $^1$HNMR (CD$_3$OD): δ 0.92 (t, J = 7.3 Hz, 3H), 1.49-1.74 (m, 2H), 2.43-2.80 (br. s, 4H), 3.30-3.40 (br. s, 2H), 7.47-7.60 (m, 2H), 7.60-7.73 (m, 2H). |
| 17 | 4-{2-[(4-bromo-2-fluorophenyl)carbamoyl]-1-propylhydrazinyl}-4-oxobutanoic acid | 16 | $^1$HNlMR (CD$_3$OD): δ 0.91 (t, J = 7.2 Hz, 3H), 1.55-1.70 (m, 2H), 2.50-2.80 (br s, 4H), 3.20-3.40 (br s, 2H), 7.28 (d, J = 8.8 Hz, 1H), 7.35 (dd, J = 1.9, 10.4 Hz, 1H), 7.85 (br s, 1H). |

Biological Data

Compounds of Formula I modulate FPR activity. For example, the data set forth in Table 6 below show that compounds of Formula I modulate FPR2 activity. HEK-Gα16 and CHO-Gα16 cells stably expressing FPR2 were cultured in (F12, 10% FBS, 1% PSA, 400 µg/ml geneticin and 50 µg/ml hygromycin) and HEK-Gqi5 cells stable expressing FPR2 were cultured in (DMEM high glucose, 10% FBS, 1% PSA, 400 µg/ml geneticin and 50 µg/ml hygromycin). In general, the day before the experiment, 18,000 cells/well were plated in a 384-well clear bottom poly-D-lysine coated plate. The following day, the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 6

| Compound IUPAC name | EC$_{50}$ nM (% Efficacy) |
|---|---|
| ethyl 3-{2-[(4-bromophenyl)carbamoyl]hydrazinyl}-3-oxopropanoate | 750 (100) |
| 3-{2-[(4-bromophenyl)carbamoyl]hydrazinyl}-2,2-dimethyl-3-oxopropanoic acid | 5212 (73) |
| 4-{2-[(4-bromophenyl)carbamoyl]hydrazinyl}-2,2-dimethyl-4-oxobutanoic acid | 602 (86) |
| methyl 2-(2-{2-[(4-bromophenyl)carbamoyl]hydrazinyl}-2-oxoethyl)-2-propylpentanoate | 46 (89) |
| 2-(2-{2-[(4-bromophenyl)carbamoyl]hydrazinyl}-2-oxoethyl)-2-propylpentanoic acid | 215 (87) |
| 4-{2-[(4-bromophenyl)carbamoyl]hydrazinyl}-2,2-diethyl-4-oxobutanoic acid | 421 (73) |
| ethyl 4-{2-[(4-bromophenyl)carbamoyl]-1-(2-methylpropyl)hydrazinyl}-4-oxobutanoate | 31 (100) |
| 4-{2-[(4-bromophenyl)carbamoyl]-1-(2-methylpropyl)hydrazinyl}-4-oxobutanoic acid | 12 (100) |
| ethyl 4-{2-[(4-bromo-2-fluorophenyl)carbamoyl]-1-(2-methylpropyl)hydrazinyl}-4-oxobutanoate | 3659 (76) |
| 4-{2-[(4-bromo-2-fluorophenyl)carbamoyl]-1-(2-methylpropyl)hydrazinyl}-4-oxobutanoic acid | 339 (99) |
| ethyl 4-[1-(2-methylpropyl)-2-{[4-(trifluoromethyl)phenyl]carbamoyl}hydrazinyl]-4-oxobutanoate | 57 (94) |
| 4-[1-(2-methylpropyl)-2-{[4-(trifluoromethyl)phenyl]carbamoyl}hydrazinyl]-4-oxobutanoic acid | 21 (98) |
| ethyl 4-oxo-4-(1-propyl-2-{[4-(trifluoromethyl)phenyl]carbamoyl}hydrazinyl)butanoate | 35 (98) |
| 4-oxo-4-(1-propyl-2-{[4-(trifluoromethyl)phenyl]carbamoyl}hydrazinyl)butanoic acid | 28 (97) |
| ethyl 4-{2-[(4-bromophenyl)carbamoyl]-1-butylhydrazinyl}-4-oxobutanoate | 34 (100) |
| ethyl 4-{2-[(4-bromo-2-fluorophenyl)carbamoyl]-1-propylhydrazinyl}-4-oxobutanoate | 34 (100) |
| 4-{2-[(4-bromo-2-fluorophenyl)carbamoyl]-1-propylhydrazinyl}-4-oxobutanoic acid | 29 (100) |

What we claim is:

1. A compound represented by Formula I:

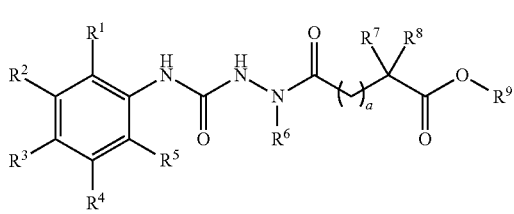

Formula I

R$^1$ is H, optionally substituted C$_{1-6}$ alkyl, C$_{1-6}$haloalkyl, optionally substituted C$_{3-8}$cycloalkyl, optionally substituted C$_{6-10}$ aryl, optionally substituted heterocycle, halogen, —OR$^{10}$, —C$_{2-6}$alkenyl, —C$_{2-6}$alkynyl, —CN, —C(O)R$^{11}$, amine, amide, urea, sulfonamide, sulfone, sulfoxide, sulfide, sulfonic acid, nitro, phosphate or phosphonic acid;

R$^2$ is H, optionally substituted C$_{1-6}$ alkyl, C$_{1-6}$haloalkyl, optionally substituted C$_{3-8}$cycloalkyl, optionally substituted C$_{6-10}$ aryl, optionally substituted heterocycle, halogen, —OR$^{10}$, —C$_{2-6}$alkenyl, —C$_{2-6}$ alkynyl, —CN, —C(O)R$^{11}$, amine, amide, urea, sulfonamide, sulfone, sulfoxide, sulfide, sulfonic acid, nitro, phosphate or phosphonic acid;

R$^3$ is H, optionally substituted C$_{1-6}$ alkyl, C$_{1-6}$haloalkyl, optionally substituted C$_{3-8}$cycloalkyl, optionally substituted C$_{6-10}$ aryl, optionally substituted heterocycle, halogen, —OR$^{10}$, —C$_{2-6}$alkenyl, —C$_{2-6}$alkynyl, —CN, —C(O)R$^{11}$, amine, amide, urea, sulfonamide, sulfone, sulfoxide, sulfide, sulfonic acid, nitro, phosphate or phosphonic acid;

R$^4$ is H, optionally substituted C$_{1-6}$ alkyl, C$_{1-6}$haloalkyl, optionally substituted C$_{3-8}$cycloalkyl, optionally substituted C$_{6-10}$ aryl, optionally substituted heterocycle, halogen, —OR$^{10}$, —C$_{2-6}$ alkenyl, —C$_{2-6}$ alkynyl, —CN, —C(O)R$^{11}$, amine, amide, urea, sulfonamide, sulfone, sulfoxide, sulfide, sulfonic acid, nitro, phosphate or phosphonic acid;

R$^5$ is H, optionally substituted C$_{1-6}$alkyl, C$_{1-6}$haloalkyl, optionally substituted C$_{3-8}$ cycloalkyl, optionally substituted C$_{6-10}$ aryl, optionally substituted heterocycle, halogen, —OR$^{10}$, —C$_{2-6}$alkenyl, —C$_{2-6}$alkynyl, —CN, —C(O)R$^{11}$, amine, amide, urea, sulfonamide, sulfone, sulfoxide, sulfide, sulfonic acid, nitro, phosphate or phosphonic acid;

R$^6$ is optionally substituted C$_{1-6}$alkyl;
R$^7$ is H or optionally substituted C$_{1-6}$alkyl;
R$^8$ is H or optionally substituted C$_{1-6}$alkyl;
R$^9$ is H or optionally substituted C$_{1-6}$alkyl;
a is 0, 1, 2 or 3;
R$^{10}$ is —OH or optionally substituted C$_{1-6}$alkyl;
R$^{11}$ is —OH, —OC$_{1-6}$alkyl or optionally substituted C$_{1-6}$alkyl;
or a pharmaceutically acceptable salt thereof.

2. The compound according to claim 1, wherein R$^6$ is unsubstituted C$_{1-6}$alkyl.

3. The compound according to claim 1, wherein a is 0 or 1.

4. The compound according to claim 1, wherein a is 1.

5. The compound according to claim 1, wherein R$^3$ is C$_{1-6}$haloalkyl or halogen.

6. The compound according to claim 1, wherein each of R$^1$ and R$^5$ is H.

7. The compound according to claim 1, wherein each of R$^7$ and R$^8$ is H.

8. The compound according to claim 1, wherein R$^1$, R$^2$, R$^4$, R$^5$, R$^7$ and R$^8$ is H.

9. The compound according to claim 1, wherein:
a is 1;
R$^1$ is H;
R$^2$ is H;
R$^3$ is C$_{1-6}$haloalkyl or halogen;
R$^4$ is H;
R$^5$ is H;
R$^6$ is unsubstituted C$_{1-6}$alkyl;
R$^7$ is H;
R$^8$ is H; and
R$^9$ is H or unsubstituted C$_{1-6}$alkyl;
or a pharmaceutically acceptable salt thereof.

10. The compound according to claim 1, selected from:

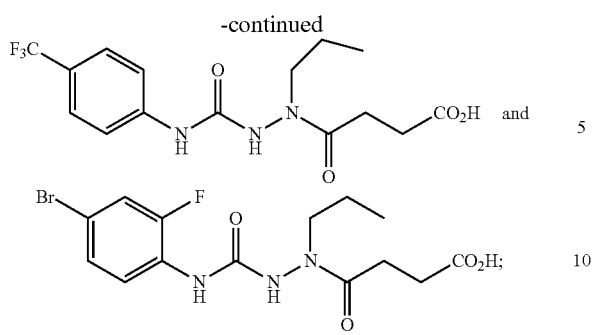
and pharmaceutically acceptable salts thereof.
11. A pharmaceutical composition comprising as active ingredient a therapeutically effective amount of a compound according to claim 1 and a pharmaceutically acceptable diluent or carrier.
* * * * *

UNITED STATES PATENT AND TRADEMARK OFFICE
CERTIFICATE OF CORRECTION

| | |
|---|---|
| PATENT NO. | : 9,663,457 B2 |
| APPLICATION NO. | : 14/679510 |
| DATED | : May 30, 2017 |
| INVENTOR(S) | : Richard L. Beard et al. |

It is certified that error appears in the above-identified patent and that said Letters Patent is hereby corrected as shown below:

On the Title Page

In item (56), in Column 2, under "Other Publications", Line 5, delete "Chemica" and insert -- Chimica --, therefor.

In the Specification

In Column 2, Line 29, delete "$C_{3-8}$ cycloalkyl," and insert -- $C_{3-8}$cycloalkyl, --, therefor.

In Column 4, Line 42, delete "3." and insert -- 3; --, therefor.

In Column 8, Line 48, delete "—"$NR^xC(O)R^y$"" and insert -- "—$NR^xC(O)R^y$" --, therefor.

In Column 10, Line 63, delete "Vogt-Koyanagi- and Harada" and insert -- Vogt-Koyanagi-Harada --, therefor.

In Column 11, Line 2, delete "telangiectasis," and insert -- telangiectasias, --, therefor.

In Column 11, Line 16, delete "(PONS)," and insert -- (POHS), --, therefor.

In Column 12, Line 16, delete "Vogt-Koyanagi- and Harada" and insert -- Vogt-Koyanagi-Harada --, therefor.

In Column 12, Line 22, delete "telangiectasis," and insert -- telangiectasias, --, therefor.

In Column 12, Line 37, delete "(PONS)," and insert -- (POHS), --, therefor.

Signed and Sealed this
Fifteenth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)

In Column 13, Line 41, delete "Vogt-Koyanagi- and Harada" and insert -- Vogt-Koyanagi-Harada --, therefor.

In Column 13, Lines 46-47, delete "telangiectasis," and insert -- telangiectasias, --, therefor.

In Column 13, Line 61, delete "(PONS)," and insert -- (POHS), --, therefor.

In Columns 19-20, Line 45, delete "2-(2 methylpropylidene)" and insert -- 2-(2-methylpropylidene) --, therefor.

In Columns 23-24, Line 19, delete "(CD$_3$OD)" and insert -- (CD$_3$OD): --, therefor.

In Columns 23-24, Line 24, delete "7.88-8.17" and insert -- 7.86-8.17 --, therefor.

In Column 23, Line 45, delete "3-{2[(4" and insert -- 3-{2-[(4 --, therefor.

In Columns 27-28, Line 8, delete "(CD3OD):" and insert -- (CD$_3$OD): --, therefor.

In Columns 27-28, Line 20, delete "4-[1-(2-methylpropyl) 2{[4-" and insert -- 4-[1-(2-methylpropyl)-2-{[4- --, therefor.

In Columns 29-30, Lines 40-42, delete "(br.," and insert -- (br --, therefor.

In Columns 29-30, Line 52, delete "(br.," and insert -- (br --, therefor.

In Column 31, Line 41, delete "FLIPR$^{Tetra}$." and insert -- FLIPR Tetra®. --, therefor.

In Column 31, Line 42, delete "MuItiPROBE" and insert -- MultiPROBE --, therefor.

In Column 32, Line 42, delete "-1 -" and insert -- -1- --, therefor.

In the Claims

In Column 32, Line 64, in Claim 1, delete "$C_{1-6}$ alkyl," and insert -- $C_{1-6}$alkyl, --, therefor.

In Column 32, Line 66, in Claim 1, delete "$C_{6-10}$ aryl," and insert -- $C_{6-10}$aryl, --, therefor.

In Column 33, Line 4, in Claim 1, delete "$C_{1-6}$ alkyl," and insert -- $C_{1-6}$alkyl, --, therefor.

In Column 33, Line 6, in Claim 1, delete "$C_{6-10}$ aryl," and insert -- $C_{6-10}$aryl, --, therefor.

In Column 33, Line 11, in Claim 1, delete "$C_{1-6}$ alkyl," and insert -- $C_{1-6}$alkyl, --, therefor.

In Column 33, Line 13, in Claim 1, delete "$C_{6-10}$ aryl," and insert -- $C_{6-10}$aryl, --, therefor.

CERTIFICATE OF CORRECTION (continued)
U.S. Pat. No. 9,663,457 B2

In Column 33, Line 19, in Claim 1, delete "$C_{1-6}$ alkyl," and insert -- $C_{1-6}$alkyl, --, therefor.

In Column 33, Line 21, in Claim 1, delete "$C_{6-10}$ aryl," and insert -- $C_{6-10}$aryl, --, therefor.

In Column 33, Line 28, in Claim 1, delete "$C_{6-10}$ aryl," and insert -- $C_{6-10}$aryl, --, therefor.